United States Patent [19]

Baudino

[11] Patent Number: 4,541,433

[45] Date of Patent: Sep. 17, 1985

[54] CARDIAC OUTPUT MONITOR

[75] Inventor: Michael D. Baudino, Coon Rapids, Minn.

[73] Assignee: Medtronic, Inc., Minneapolis, Minn.

[21] Appl. No.: 616,366

[22] Filed: Jun. 1, 1984

[51] Int. Cl.⁴ .......................... A61B 5/02; A61B 10/00
[52] U.S. Cl. ..................................... 128/668; 128/691
[58] Field of Search ............... 128/642, 784–786, 128/419 P, 661, 663, 668, 673, 675, 691, 774

[56] References Cited

U.S. PATENT DOCUMENTS

| | | | |
|---|---|---|---|
| 3,661,146 | 5/1972 | Peronneau et al. | 128/663 |
| 4,141,365 | 2/1979 | Fischell et al. | 128/419 R X |
| 4,294,258 | 10/1981 | Bernard | 128/642 X |
| 4,313,448 | 2/1982 | Stokes | 128/785 |
| 4,355,643 | 10/1982 | Laughlin et al. | 128/663 |
| 4,432,372 | 2/1984 | Monroe | 128/675 |

*Primary Examiner*—Kyle L. Howell
*Assistant Examiner*—Francis J. Jaworski
*Attorney, Agent, or Firm*—Reed A. Duthler; Joseph F. Breimayer; John L. Rooney

[57] ABSTRACT

A cardiac output monitor of the type including an ultrasound crystal for use as a doppler flowmeter. The monitor is designed for mounting directly to a blood vessel, and is provided with a novel fixation apparatus which allows for easy and secure attachment to the blood vessel. The fixation apparatus includes two parallel fixation wires especially adapted for location in the blood vessel wall, without the danger of piercing the vessel wall.

5 Claims, 5 Drawing Figures

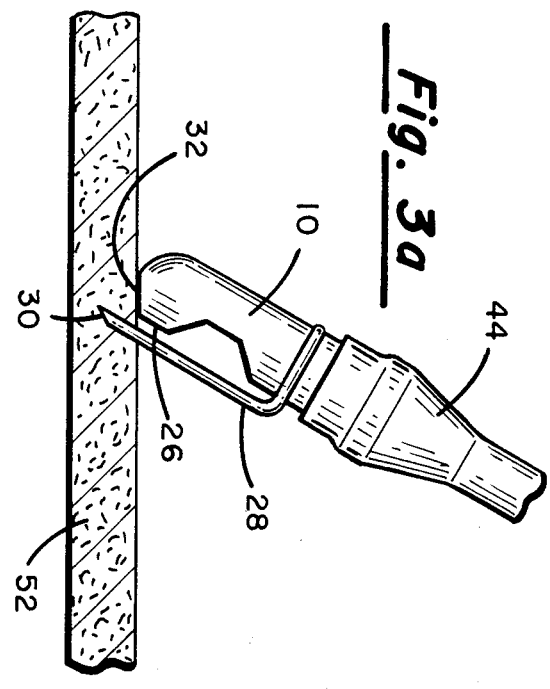
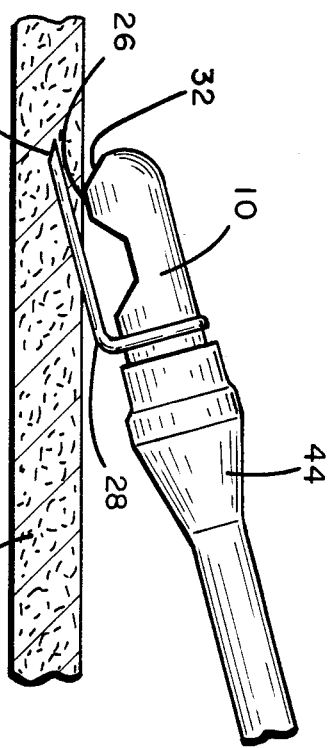
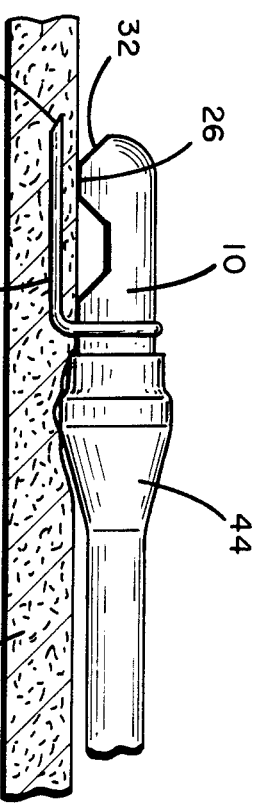
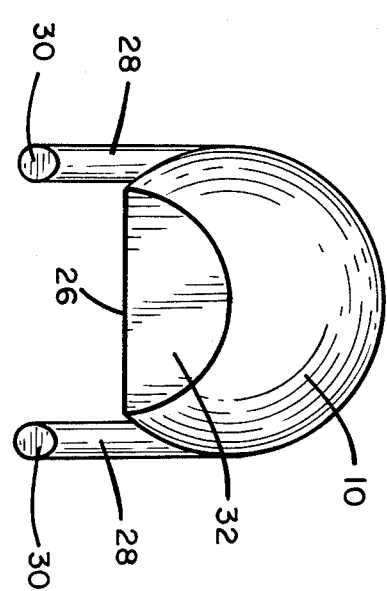

CARDIAC OUTPUT MONITOR

BACKGROUND OF THE INVENTION

This invention relates generally to the field of electro-medical transducers and more particularly to attachment of medical transducers to blood vessels.

In the past, medical researchers have utilized ultrasound crystals in experimental settings in various combinations and arrangements in order to monitor blood flow or measure cardiac stroke volume. In some cases, such measurements were accomplished by use of ultrasound crystals mounted on catheters passed within blood vessels and veins, and in other cases crystals have been attached to the exterior of the heart or blood vessels. Such attachment has in the past involved suturing the transducer bearing the ultrasound crystal directly to the heart or blood vessel, or suturing a loop or pocket to the heart or blood vessel for retaining the transducer. These procedures are time consuming and difficult. More importantly, the requirement of suturing poses a serious risk, especially in the context of attachment of the transducer to a blood vessel such as the aorta, which typically has a wall thickness of less than 3.2 mm.

The present invention provides a transducer head adapted for use as a doppler flowmeter, which avoids complications and problems due to the use of sutures as an attachment method. The transducer head of the present invention employs two parallel fixation wires which serve to affix the transducer to the desired blood vessel without danger of piercing its wall. The fixation wires also allow for a transducer which requires considerably less time and effort to use than previous transducers which had to be sutured to the blood vessel.

The present invention is believed particularly useful in monitoring blood flow during open heart surgery. Because time and safety considerations are paramount during open heart surgery, it is desirable that diagnostic tools used in conjunction with such surgery not pose significant additional time requirements or additional risks to the patient. The present invention by means of its novel fixation apparatus provides a transducer which meets this criteria, and moves the ultrasound blood flowmeter from the laboratory of the medical researcher to the operating room of the clinician.

BRIEF DESCRIPTION OF THE DRAWINGS

FIG. 2 shows a front plan view of a transducer head according to the present invention.

FIGS. 3a, 3b and 3c illustrate the attachment of the transducer head to a blood vessel.

DETAILED DESCRIPTION OF THE INVENTION

Figure 1:
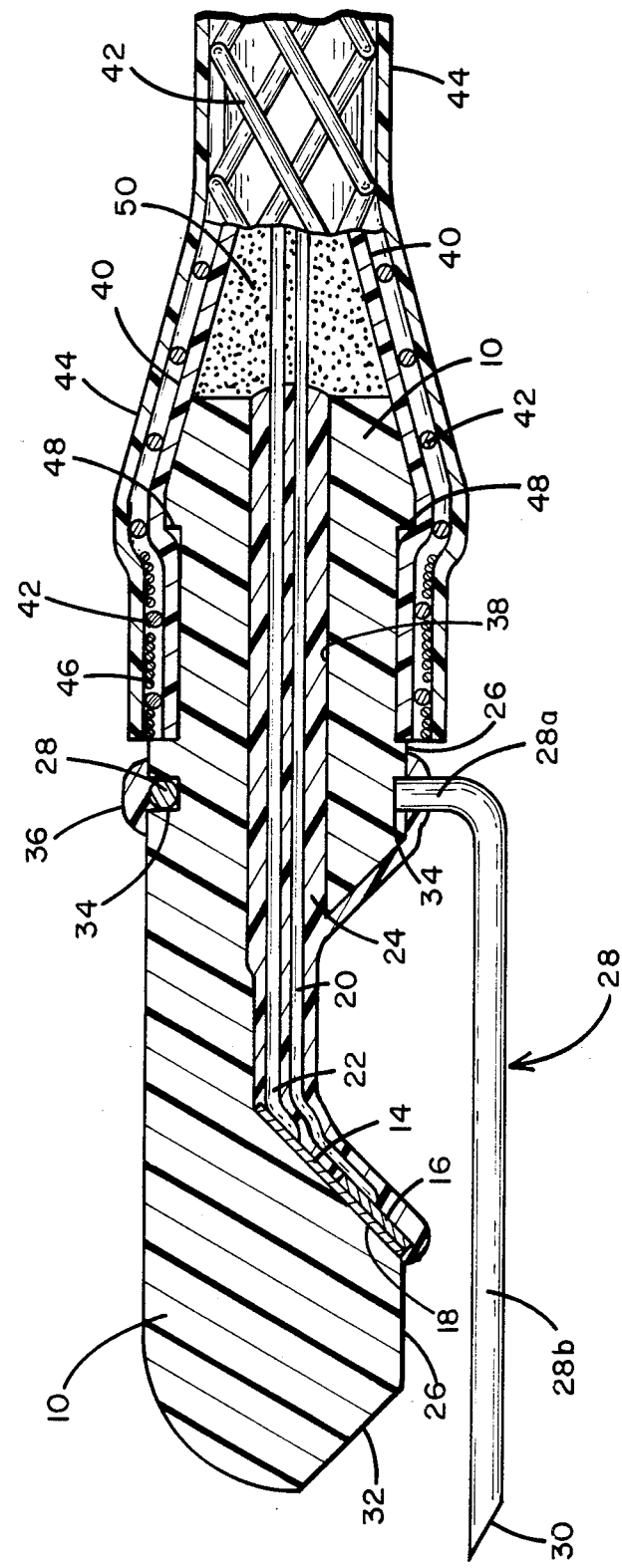
FIG. 1 shows a side sectional view of a transducer head according to the present invention.

FIG. 1 shows a side sectional view of a transducer head according to the present invention. The transducer consists of a transducer head 10 which may be fabricated of any appropriate, biologically inert plastic such as polysulfone, Teflon ® or Delrin ®. Transducer body 10 is provided with a recess in which the ultrasound crystal 16 is mounted. Ultrasound crystal 16 is mounted on base plate 14 along slanted wall 18, at a predetermined angle to the ventral surface 26 of the transducer head. In the illustrated embodiment, this angle is approximately 45 degrees, however, other angles may be used. Power to and signals from the transducer are carried by conductors 20 and 22, which are electrically coupled to opposite sides of crystal 16. Connection to the upper surface of crystal 16 is effected by way of conductor 22 which is soldered to base plate 14 which is fabricated of titanium coated with a thin layer of gold on its exposed surface. Crystal 16 is provided with a thin layer of chromium plated with a thin layer of gold on both its upper and lower surfaces. Crystal 16 is attached to base plate 14 by means of a very thin layer of epoxy. Conductor 20 is soldered directly to the gold metallized lower surface of crystal 16. Crystal 16, conductors 20 and 22, and base plate 14 are all encapsulated in hysol epoxy 24, which serves to protect these structures and serves as an insulative layer. The ventral surface 26 of the transducer is flattened, and is intended to lie against the outer surface of the blood vessel.

Fixation wires 28, of which only one is visible in this illustration, are each shown to include a short vertical segment 28a extending perpendicular to the ventral surface 26 of the transducer for approximately 0.05 inches. The length of this segment may vary, but it must extend a distance less than the thickness of the wall of the blood vessel to which it will be attached. For purposes of this application, the thickness of the vessel wall includes both the thickness of the muscular wall of the vessel as well as the thickness of any fascia tissue covering the vessel. A horizontal segment 28b extends distally parallel to the ventral surface. At their distal ends, fixation wires 28 terminate in bevels 30, which as illustrated, are preferably approximately of 30 degrees. The distal end of transducer head 10 is also provided with a beveled surface 32, which may have an angle of approximately 45 degrees to the ventral surface 26, and serves to assist the physician in determining the proper angle of insertion of the fixation wires 28. In addition, beveled surface 32 limits the insertion depth. It is thus necessary that the distal ends of fixation wires 18 extend a distance perpendicular to beveled face 32 less than the thickness of the wall of the blood vessel to which the transducer head will be attached. Fixation wires 28 as shown are fabricated from a 0.014" stainless steel wire, wrapped around transducer head 10 within a groove 34, and maintained in place by means of epoxy 36. Alternatively, fixation wires 28 could be insert molded into transducer head 10.

Conductors 22 and 20 proceed proximally within a central bore 38 within transducer head 10, and extend proximally from that point through a tubular lead body. The lead body includes a plastic inner tubular sheath 40, which is slid over the proximal end of transducer head 10. Surrounding tubular sheath 40 is braided metal tubing 42 which provides tensile strength to allow removal of the transducer by pulling on the lead body. Braided tubing 42 is in turn surrounded by an outer tubular sheath 44. Tubular sheath 40 and braided tubing 42 are affixed to the proximal end of transducer head 10 by means of a tightly wrapped wire 46, which prevents the lead body from sliding proximally, off of shoulder 48. Within inner tubing 40, silicone medical adhesive 50 serves as a strain relief for the exit point of conductors 20 and 22.

FIG. 2 shows a front plan view of the transducer head, illustrating the relationship of the fixation wires 28 and ventral surface 26. The combination of flattened ventral surface 26 and the parallel wires 28 prevent any rotational or rocking motion of the transducer head after attachment. These and other advantages of the present invention are more fully appreciated in conjunction with the following explanation of its operation.

FIG. 3a shows the initial placement of the transducer at the desired location point on blood vessel. Initially, fixation wires 28 are inserted in the blood vessel wall 52, with beveled face 32 parallel to wall 52 and the transducer is advanced until beveled face 32 lies against wall 52.

FIG. 3b shows the transducer head pivoted to a position close to parallel to the surface of the blood vessel wall 52, and ready for final location. The angle of the transducer head at this point is preferrably less than 30°, so that the bevels 30 of the wires 28 properly perform their function. At this point, the transducer head may be moved distally, allowing fixation wires 28 to progress within the wall of the blood vessel until completely embedded. During this procedure, the beveled edges 30 of the fixation wires 28 provide two useful functions. First, by acting as knife edges, they facilitate passage of the wires within the blood vessel wall. Second, because the bevels face ventrally, they provide a planing action which inhibits the tendency the wires would otherwise have to pull away from the ventral surface of the transducer head during sliding due to the necessity of insertion at an angle. This planing action is valuable as it assists in preventing fixation wires 28 from piercing the wall of the blood vessel and from acting to unduly compress the tissue of the blood vessel wall between the ventral surface of the transducer head and fixation wires 28. The general downward force exerted by the physician during the attachment of the transducer, coupled with the rigidity of the wires is sufficient to prevent bevel 30 from causing wires 28 to resurface through the exterior of the vessel wall.

FIG. 3c shows the transducer head in its final attachment position on the blood vessel wall ready for use. The combination of the flattened ventral surface 26 and the parallel fixation wires 28 maintains the transducer in a stable location, not susceptible to any twisting or turning during use which might cause inaccuracies in flow measurement. Following use, the transducer is easily removed by simply pulling it in a proximal direction, sliding fixation wires 28 out of the vessel wall.

What is claimed is:

1. A biomedical transducer for mounting to the wall of a blood vessel, comprising:
   a transducer head having a proximal end, a distal end, and a ventral surface;
   a transducer, mounted to said transducer head;
   two fixation wires each having a first segment extending from said ventral surface of said transducer head for a first distance less than the thickness of the wall of said blood vessel and a second segment extending for a second distance, parallel to the ventral surface of said transducer head and terminating in ventrally facing bevels, wherein said second segments of said fixation wires extend distal to said first segments of said fixation wires and extend from the distal end of said transducer head for a distance less than the thickness of the wall of said blood vessel; and
   a transducer lead means coupled to the proximal end of said transducer head, for coupling said transducer to monitoring equipment.

2. A biomedical transducer for mounting to the wall of a blood vessel, comprising:
   a transducer head having a proximal end, a distal end, and a ventral surface;
   a transducer, mounted to said transducer head;
   two fixation wires each having a first segment extending from said ventral surface of said transducer head for a first distance less than the thickness of the wall of said blood vessel and a second segment extending for a second distance, parallel to the ventral surface of said transducer head, wherein said second segments of said fixation wires extend distal to said first segments of said fixation wires and extend from the distal end of said transdueer head for a distance less than the thickness of the wall of said blood vessel; and
   a transducer lead means coupled to the proximal end of said transducer head, for coupling said transducer to monitoring equipment.

3. A biomedical transducer according to claim 1 or claim 2 wherein said distal end of said transducer head is provided with a beveled surface, and wherein said second segments of said fixation wires extend in a direction perpendicular to said beveled surface a distance less than the thickness of the wall of said blood vessel.

4. A biomedical transducer according to claim 1 or claim 2 wherein said ventral surface of said transducer head is flattened, and wherein said first segments of said fixation wires extend perpendicular to said ventral surface of said transducer head.

5. A biomedical transducer according to claim 4 in which said transducer head is provided with an angled wall, having a predetermined angle relative to said ventral surface of said transducer head, and wherein said transducer comprises an ultrasound crystal, mounted to said angled wall of said transducer head such that when said ventral surface of said transducer head is located against said wall of said blood vessel, said ultrasound crystal is mounted at said predetermined angle to the wall of said blood vessel.

* * * * *